United States Patent [19]

Saucy

[11] 3,984,427
[45] Oct. 5, 1976

[54] PREPARATION OF VINYL LACTONES AND CORRESPONDING MANNICH BASES
[75] Inventor: Gabriel Saucy, Essex Fells, N.J.
[73] Assignee: Hoffmann-La Roche Inc., Nutley, N.J.
[22] Filed: June 18, 1969
[21] Appl. No.: 834,547

Related U.S. Application Data
[63] Continuation-in-part of Ser. No. 778,314, Nov. 22, 1968, Pat. No. 3,700,661.

[52] U.S. Cl. .................... 260/307 H; 260/247.2 B; 260/247.5 E; 260/293.67; 260/293.88; 260/293.89; 260/326.36; 260/326.42; 260/247.7 R; 260/326.5 D; 260/326.5 J; 260/333; 260/345.8; 260/345.9; 260/347.4; 260/347.8; 260/488 J; 260/594; 260/247.7 T
[51] Int. Cl.² .................................. C07D 261/08
[58] Field of Search............ 260/307 H, 345.9, 594, 260/333, 345.8, 347.4, 347.8, 488 J, 247.2 B, 247.5 E, 247.7 A, 293.67, 293.88, 293.89, 326.36, 326.42, 326.5 D, 326.5 J

[56] References Cited
UNITED STATES PATENTS
3,624,144   11/1971   Wendler et al. .................... 260/521

OTHER PUBLICATIONS

Houben–Weyl–"Methoden der Organischen Chemie" Vierte Auflage–Sauerstoff Verbingungen 1–6/23 p. 826 (1963).

*Primary Examiner*—Raymond V. Rush
*Attorney, Agent, or Firm*—Samuel L. Welt; George M. Gould

[57] ABSTRACT

Vinyl ketones and Mannich-bases obtained therefrom are useful as intermediates in the total synthesis of steroids having valuable pharmacological properties. These compounds are prepared by the low temperature reaction of a vinyl Grignard e.g., vinyl magnesium chloride with substituted $\gamma$, $\delta$ or $\epsilon$ lactones followed, if desired, by reaction of the vinyl ketone obtained with a primary or secondary amine. Particular compounds prepared by this procedure include 2-(2-substituted aminoethyl)-6-substituted-2-hydroxy-tetrahydropyrans and the tautomers thereof.

17 Claims, No Drawings

PREPARATION OF VINYL LACTONES AND CORRESPONDING MANNICH BASES

RELATED APPLICATIONS

The present application is a continuation-in-part of U.S. patent application Ser. No. 778,314, filed Nov. 22, 1968, now U.S. Pat. No. 3,700,661, entitled "Total Steroid Synthesis Employing Substituted Isoxazole Derivatives", inventors, Gabriel Saucy and John William Scott.

BRIEF DESCRIPTION OF THE INVENTION

The present invention relates to an improved process for the preparation of compounds of the following formula

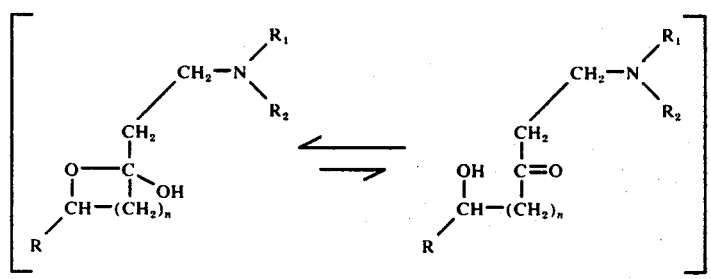

I where R is hydrogen, alkyl or substituted alkyl; $R_1$ taken independently is hydrogen or lower alkyl; $R_2$ taken independently is lower alkyl or aralkyl; $R_1$ and $R_2$ taken together with the adjacent nitrogen atom form a 5 or 6 membered saturated heterocyclic ring including at the most one further hetero atom selected from the group consisting of nitrogen and oxygen and n is an integer from 2 to 4.

The first step in the process of the present invention involves the unexpected addition of a single mol equivalent of vinyl Grignard to a lactone compound of the following formula

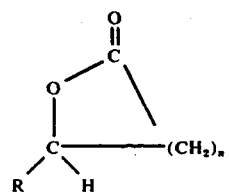

II where R and n are as above.

The resulting vinyl ketone which is prepared in the aforesaid reaction corresponds to the following formula

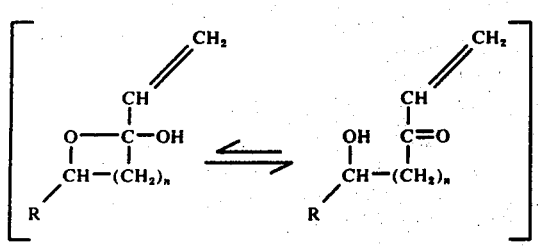

III where R and n are as above.

The vinyl magnesium halides which are useful as the Grignard reagent for the above reaction are preferably the chloride, bromide and iodide. The reaction is conducted in the presence of an organic solvent, preferably an etheric reaction medium such as diethyl ether, diisopropyl ether, tetrahydrofuran, dioxane and the like. Surprisingly, it has been found that when the reaction is conducted at low temperature conditions the carbonyl group of the thus-obtained vinyl-hydroxy compound of formula III is stable to further reaction with Grignard reagents. Thus, the reaction is suitably effected at a temperature below about 0° C., e.g., at a temperature of from about −90° C. to about 0° C. and preferably at a temperature of from about −70° C. to about −30° C. The order of addition of the reactions is not critical although it is generally preferred to add the vinyl magnesium halides to the lactones. Use of temperatures above about 0° C. must be avoided in the reaction step since compounds of formula III have been observed to undergo a secondary reaction with addition of another vinyl group to yield divinyl alcohols and the desired compounds of formula III are either not formed or are available only in very minor yields.

The compounds of formula III are somewhat unstable particularly upon exposure to acid or base and because of the susceptibility of the vinyl group to oxidation. It is therefore desirable although not essential that these compounds be converted to more stable variants, most preferably by reacting these compounds with an amine of the following formula

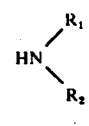

IV where $R_1$ and $R_2$ are as above.

In a most preferred embodiment the reaction of the amines of formula IV with the compounds of formula III is conducted in situ in the reaction medium from which the compounds of formula II were prepared, preferably at a temperature in the range of from about −10° C. to 30° C., most preferably at about room temperature. The resulting Mannich-base compound corresponds to the desired compounds of formula I above.

It should be noted that compounds of formulae I and III are believed to exist in solution in the tautomeric forms as indicated by the respective sub-formulae. The cyclic structure for the compounds of formula I and the open structure for the compounds of formula III are believed to be the lower energy form and are thus favored in the tautomeric equilibrium under most conditions. Evidence for the existence of the open form for compound V and the closed form of compound IV is observed in the infrared wherein carbonyl and hydroxyl stretching adsorption peaks respectively are observed. The absolute structure of these compounds is not considered to be critical to the practice of the present invention.

As used herein the term "alkyl" comprehends saturated branched or unbranched hydrocarbon groups having from 1 to 15 carbon atoms. The term "lower alkyl" is meant to include alkyl groups having from 1 to 7, preferably 1 to 4 carbon atoms. Examples of suitable lower alkyl groups include methyl, ethyl, propyl, isopropyl, butyl, tertiary butyl, etc. The term "aralkyl" includes phenyl-lower alkyl radicals such as, for example, benzyl groups. The 5 or 6 membered saturated heterocyclic rings include, for example, the pyrrolidinyl, piperidinyl and morpholino groups, among others. The term "substituted alkyl" comprehends an alkyl group substituted with one or more of the following: oxo group, protected oxo group, such as, for example, a ketal or thioketal, a hydroxy group, a protected hydroxy group, such as for example, a lower acyloxy or lower alkoxy group or a heterocyclic group such as, for example, an isoxazole group.

In one preferred embodiment of the present invention R is alkyl, preferably lower alkyl and most preferably an ethyl group. Preferred embodiments wherein R is substituted alkyl include, for example, a pentyl group containing the following substituents in the δ-position: oxo and protected oxo groups, e.g., ketals and thioketals, which include, for example, lower alkylenedioxy and arylenedioxy ketals, e.g., 1,2-ethylenedioxy, 2,3-butylenedioxy, 2,2-dimethyl-1,3-propylenedioxy, 1,2-ethylenedimercapto, phenylenedioxy, 1,2-naphthylenedioxy, 2,3-naphthylenedioxy, or the like; and hydroxy or protected hydroxy groups, such as acyloxy, preferably acetyloxy or alkoxy, preferably tertiary alkoxy, most preferably t-butoxy; or an ethyl group bearing on the β-carbon atom an isoxazole ring of the following formula:

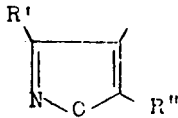

where R' is lower alkyl or hydrogen and R'' is lower alkyl, lower alkylaryl, aralkyl or hydrogen.

Illustrative examples of isoxazoles of formula V include the following groups: 3,5-dimethyl-4-isoxazolyl, 3-methyl-4-isoxazolyl, 3,5-diethyl-4-isoxazolyl, 5-ethyl-4-isoxazolyl, 3-methyl-5-phenyl-4-isoxazolyl, 3-methyl-4-isoxazolyl and the like.

The value of n in a most preferred aspect of the present invention is 3. The amines of formula IV useful in the practice of the present invention may be primary or secondary amines. Suitable primary amines include, for example, the lower alkylamines, such as methylamine, ethylamine, propylamine, n-butylamine, hexylamine, etc., preferably n-butylamine; aralkylamines, such as α-methylbenzylamine or amines of complex molecules such as, for example, dehydroabietylamines. The secondary amines most preferably include di-lower alkylamines, which may contain additional substituents on the alkyl groups, e.g., phhenyl; or cyclic amines having 5 or 6 membered saturated rings. Examples of di-lower alkylamines include dimethylamine, diethylamine, methylethylamine, desoxyephedrine (2-methyl-1-phenylethylamine), etc., with diethylamine being of greatest preference. Examples of cyclic amines include pyrrolidine and piperidine, while morpholine is an example of a cyclic amine having an additional heterocyclic atom.

The lactones of formula II which are the starting material for the practice of the present invention are readily prepared, where R is other than alkyl substituted with an isoxazole moiety, by reacting a dialdehyde of the formula

where n is as above
with the desired alkyl or substituted alkyl Grignard reagent, e.g., the magnesium halide of such alkyl or substituted alkyl compounds, most preferably the magnesium chloride. The resulting lactol may then be oxidized to yield the desired lactone of formula II.

The Grignard reagent employed in the preparation of compounds of formula II are all readily derived from the corresponding alkyl halides or substituted alkyl halides. In particular, the 4-substituted pentylmagnesium halides can be obtained from 1-halo-4-pentanones or 1-halo-4-pentanols. For example, a 1-halo-4-pentanone can be converted to its ketal by reaction with an alkane diol, phenylene diol or alkane dithiol in known manner and the ketal subsequently reacted with magnesium in known manner to produce the starting Grignard reagent. Finally, a 1-halo-4-pentanol can be reacted directly with magnesium to produce a hydroxyl-containing Grignard reagent, or first etherified in known manner and then reacted with magnesium to produce an esterified Grignard reagent.

The lactols produced in accordance with the above description are generally recovered in the form of a racemic mixture. Because the products of the process of the present invention are of special utility as starting materials for the total synthesis of steroids, it is preferred, although not essential, that these racemic mixtures be resolved into their optically active antipodes to serve as intermediates for the preparation of optically active enantiomers of compounds of formula II. This resolution can be carried out by any suitable method. For example, the lactol can be reacted with a dicarboxylic acid, such as oxalic, malonic, succinic, butyric, adipic, or phthalic acid, to form a half-ester. The half-ester is then reacted with an optically-active base, such as brucine, ephedrine, or quinine to produce a diastereomeric salt. The salts, after separation, are then reconverted to the optically-active alcohol. Alternatively, the lactol can be reacted with an optically-active acid, for example, camphorsulfonic acid. The resulting diastereomeric esters are then separated and reconverted to the optically active alcohols.

The preparation of 6-substituted tetrahydropyran-2-ols is discussed in greater detail in U.S. Patent application Ser. No. 633,693, filed Apr. 26, 1967, entitled, "6-Substituted Tetrahydropyran-2-ols and Process for their Production", inventors, David A. Andrews and Gabriel Saucy and now abandoned.

The conversion of the aforesaid lactols, such as for example, the 6-substituted tetrahydropyran-2-ols into compounds of formula II may be readily accomplished by careful oxidation. This oxidation may be effected with an oxidizing agent such as manganese dioxide or the like in an inert organic solvent, such as an aromatic hydrocarbon, e.g., toluene, benzene or xylene or a halogenated hydrocarbon such as methylene chloride, chloroform, 1,2-dichloroethane, etc. at room temperature.

Compounds of formula II wherein R is an isoxazole substituted alkyl group may be prepared in accordance with the following reaction scheme:

wherein R', R'' and $n$ are as above; and X is an inorganic anion derived from a mineral acid, $R_1$, $R_2$ and $R_3$ independently are selected from the group consisting of lower alkyl, phenyl, and phenyl-lower alkyl, preferably phenyl and $R_{10}$ is lower alkyl.

Substituted hydroxy isoxazole compounds of formula A of the Reaction Scheme can be conveniently obtained by means known in the art from the corresponding 3,5-disubstituted-4-carboxyisoxazoles. [Cf., G. Stork et al., J. Chem. Soc. 89, 5461 (1967)].

The alcohols of formula A are converted to the compounds of formula B, in accordance with the Reaction Scheme. Suitably, the anion represented by X is an inorganic anion derived from a mineral acid, e.g., chloride, bromide, iodide, sulfate or the like. A preferred anion is chloride in which case the compounds

REACTION SCHEME

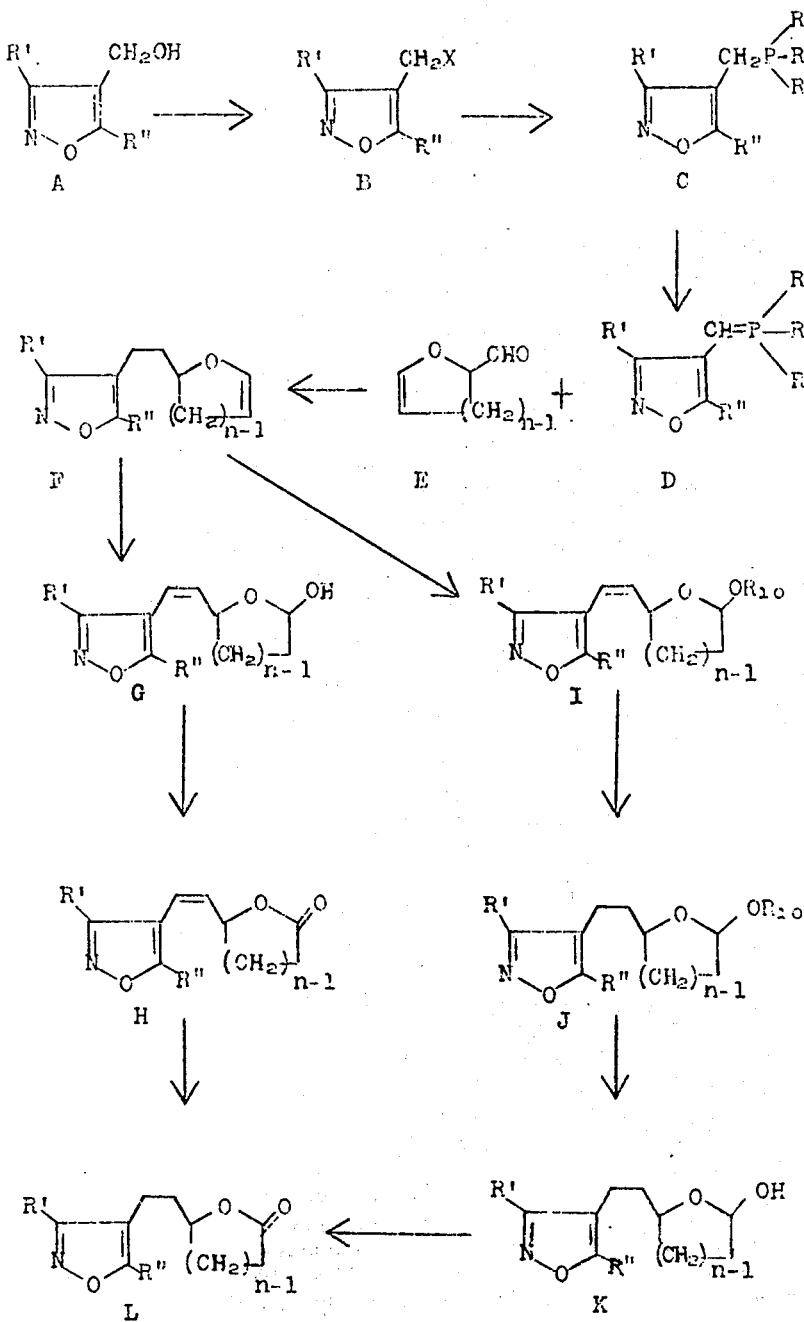

of formula B can be obtained by the reaction of the alcohols of formula A with, for example, thionyl chloride in methylene chloride solvent at a temperature of approximately −10° C. to +30° C.

The phosphonium salts of formula C can be obtained by treatment of the halide B with the desired phosphine reagent such as, for example, triethylphosphine, triphenylphosphine, bis-(diethyl)-phenyl-phosphine and the like in a suitable solvent preferably a hydrocarbon, e.g., benzene, toluene, or the like at the reflux temperature of the solvent. The reaction is preferably conducted under a nitrogen atmosphere.

The ylids of formula D can be generated from the compounds of formula C by treatment of the compounds of the formula C with an acid binding agent, such as for example, with an alkali metal-lower alkoxide, for example, sodium methoxide; an alkali metal hydroxide such as sodium hydroxide; or an alkali metal hydride such as sodium hydride in a suitable solvent, preferably dimethylsulfoxide. [Cf., R. Greenwald et al., J. Org. Chem. 28, 1128, (1963)].

The thus obtained Wittig reagent of formula D can be employed to prepare the vinyl pyran compounds of formula F as schematically represented in the Reaction Scheme by reacting the compounds of formula D with a compound of formula F., e.g., acrolein dimer. The reaction is suitably conducted at a temperature between room temperature and 150° C. It has been found that a preferable temperature range in which to conduct the reaction is between 65° and about 75°. The quantity of reactants used is not critical and an excess of either can be used. However, it has been found advantageous to use an essentially equimolar ratio of reactants. This reaction is suitably effected in a solvent such as, for example, ethers, e.g., lower alkyl ethers such as dioxane and tetrahydrofuran; aromatic hydrocarbons such as benzene and xylene; di-lower alkyl-lower alkanoylamides such as dimethylformamide and dimethylacetamide; and dimethylsulfoxide. A preferred solvent for this reaction is dimethylsulfoxide. Alternatively, the phosphonium salts of formula C can be reacted directly with acrolein dimer by generating in situ the ylid of formula D by adding the acid binding agent to the reaction system.

Conversion of the Wittig adduct of formula F to the heptanoic acid lactones of formula L can be accomplished via separate routes as exemplified in the Reaction Scheme.

Thus, one method for preparing the lactones of formula L comprises hydrating the vinyl pyrans of formula F to the hemiacetals of formula G. The hydration is suitably effected at room temperature in an inert organic solvent such as tetrahydrofuran, dioxane, or a di-lower alkyl ketone such as acetone by means of a mineral acid, preferably hydrochloric acid or sulfuric acid. The hemiacetals can be converted to the vinyl lactones of formula H by oxidizing with a suitable oxidizing agent, preferably manganese dioxide in a hydrocarbon solvent, preferably benzene at room temperature.

The heptanoic acid lactones of formula L are obtained by selective hydrogenation of the heptanoic acid lactones of formula H. A significant aspect of the instant synthesis lies in the selective hydrogenation of olefinically unsaturated compounds containing an isoxazole moiety without substantially attacking the isoxazole group. It is essential that this hydrogenation reaction be conducted so as to avoid any significant hydrogenation of the isoxazole moiety. The hydrogenation is thus suitably conducted in the presence of a noble metal catalyst, such as palladium, platinum, rhodium, etc. under mild reaction conditions, viz., without the addition of heat and substantially at atmospheric pressure. The noble metal catalyst can be utilized with or without a carrier and if a carrier is used, conventional carriers are suitable. It is preferred to use a catalyst comprising palladium on a carbon carrier. The ratio of catalyst to substrate is not critical and can be varied. However, it has been found advantageous to use a weight ratio of catalyst to substrate from about 1:5 to about 1:100. Especially preferred is a ratio of 1:25. The hydrogenation is suitably effected in the presence of an inert organic solvent, optionally in the presence of acids or mono, di or trialkyl amines. Suitable solvents which may be employed are ethers, such as diethylether or tetrahydrofuran; lower alkyl esters of lower alkanoic acids such as ethyl acetate; and aromatic hydrocarbons such as toluene or benzene and the like. It is especially preferred to conduct the hydrogenation using an ethyl acetate solvent.

Alternatively, lactones of the formula L may be prepared from the vinyl pyrans of formula F by first preparing the hemiacetals of formula K by an alcohol addition process. The conversion is suitably effected using a mineral acid, preferably sulfuric acid, in the presence of a lower alcohol, preferably ethanol, which serves both as a solvent and a source for the alkoxy protecting group.

The hemiacetals of formula K can be prepared from the acetals of formula I by first selectively hydrogenating the acetals of formula J employing similar hydrogenating conditions to that which were used to effect the hydrogenation of the compounds of formula H to the compounds of formula L as described above and subsequently removing the alkoxy protecting group by means of aqueous mineral acid, preferably sulfuric acid in an inert organic solvent, preferably an ether such as dioxane and tetrahydrofuran, or a di-lower alkyl ketone such as acetone. This latter reaction can be conveniently carried out at room temperature. The lactones of formula L are then obtained by oxidation of the compounds of formula K in the same manner described above for formation of compounds of formula H, such as for example, treatment with manganese dioxide in a hydrocarbon solvent.

More complete particulars of each of the aforesaid reactions plus additional reaction pathways to lactones L may be found in U.S. Patent application Ser. No. 778,314, filed Nov. 22, 1968, now U.S. Pat. No. 3,700,661, entitled, "Total Steroid Synthesis Employing Substituted Isoxazol Derivatives", inventors Gabriel Saucy and John William Scott.

The compounds of formula I are useful as intermediates in the total synthesis of steroids having valuable pharmacological properties. Thus, for example, compounds of formula I where R is other than alkyl substituted with an isoxazole ring or alkyl substituted with arylenedioxy may be converted into known steroids, e.g., steroids of the series 9$\beta$,10$\alpha$-androst-4-en-3-one by procedures now well known in the art, see for example, Belgian Pat. No. 698,390 published Nov. 13, 1967.

The conversion of arylenedioxy substituted derivatives of formula I compounds into known steroids, e.g., 19-norandrost-4-en-3,17-dione is described in U.S. patent application Ser. No. 824,319 filed May 13, 1969, entitled, "Aryl Ketals of Polycyclic Oxo Compounds and Processes", inventors Michael Rosenberger and Gabriel Saucy now U.S. Pat. No. 3,544,600, issued Dec. 1, 1970, this disclosure being incorporated by reference.

Compounds of formula I wherein R is alkyl substituted with an isoxazol group may be converted into steroids of known pharmacological utility by procedures described in the aforesaid U.S. patent application Ser. No. 778,314, whose disclosure is incorporated herein by reference.

Compounds of formula I wherein n is 2 or 4 may be converted into steroids having known valuable pharmacological properties wherein the B ring contains 4 or 6 members, e.g., B-nor and B-homosteroids respectively by procedures directly analogous to the schemes disclosed herein by utilizing starting materials having n equal to 2 or 4.

In the claims, all compounds shall be construed to include, independently, the racemic form of the compound and independently, each enantiomeric form, i.e., the d and l configurations unless specifically indicated otherwise.

The following examples are illustrative but not limitive of the invention. All temperatures are stated in degrees Centigrade. Infrared, ultraviolet and nuclear magnetic resonance spectra were taken were consistent with exemplified structures.

EXAMPLE 1

A solution containing 3.2 g. 5-ethyl-5-hydroxy-valeric acid lactone in 16 ml. of tetrahydrofuran (which had been filtered through alumina grade I before use) was cooled to −45° and, with rapid agitation, there was added 12.3 ml. of vinyl magnesium chloride solution (21.2 percent in tetrahydrofuran). After stirring for an additional 15 minutes at −45°, 6.4 ml. of diethylamine was added. The reaction mixture was then poured onto a mixture of ice, ammonium chloride and ether. After separation, the aqueous phase was extracted with three portions of ether and the combined organic phases were extracted with two portions of saturated sodium chloride solution. The organic phases were dried over sodium sulfate in the presence of 6.4 ml. of diethylamine. Evaporation of the solvent, after filtration, yielded 5.6 g. of a yellow oil which consisted of crude 2-(2-diethylaminoethyl)-6-ethyl-2-hydroxy-tetrahydropyran.

EXAMPLE 2

A solution containing 171 ml. of vinyl magnesium chloride (25.4 per cent in tetrahydrofuran) was added to a solution of 32 g. of S-(−)-5-ethyl-5-hydroxy-valeric acid lactone (prepared by the microbiological reduction of 5-keto-heptanoic acid by the procedure described in U.S. Pat. No. 3,076,750, issued Feb. 5, 1963) in 100 ml. of tetrahydrofuran at −45° during a period of 10–15 minutes. The reaction mixture was then cooled to −65° and treated cautiously with 10 ml. of methanol so that the temperature did not exceed −50°. After pouring the reaction mixture onto a mixture of ice, ammonium chloride, acetic acid and ether, the organic phase was separated and the aqueous phase extracted with two portions of 350 ml. of ether. The organic phase was washed with two portions of sodium bicarbonate solution (2 × 100 ml. saturated). The combined organic phases were then treated with sodium sulfate and 32 ml. of diethylamine. Filtration and evaporation of the solvent yielded 51.5 g. of a yellow oil which was purified by dissolving it in ether, (500 ml.) and extracting with three portions (1 = 200 ml., 2 = 70 ml., 3 = 70 ml.) of 1N hydrochloric acid. The aqueous phases were combined and washed with two portions of ether (350 ml. each), then neutralized with 37 ml. of 10N sodium hydroxide solution in the presence of 500 ml. of ether. After extraction of the separated aqueous phase with two portions (300 ml. each) of ether, the combined organic phases were washed with sodium chloride solution and dried over sodium sulfate. Evaporation of the solvent yielded 42.4 g. of pure S-(−)-2-(2-diethylaminoethyl)-6-ethyl-2-hydroxy-tetrahydropyran as an oil.

EXAMPLE 3

A solution containing (±)-2-[3-(6-oxo-2-tetrahydropyranyl)propyl]-2,4,5-trimethyl-1,3-dioxolane (40 g.) in 200 ml. of tetrahydrofuran was cooled to −45° under nitrogen. A 2.12 molar solution of vinyl magnesium chloride in tetrahydrofuran was added dropwise at −45° to −50° over 10 minutes, stirring being continued at −55° to −60° for an additional 35 minutes. Then 10 ml. of methanol was added dropwise and the reaction mixture was poured onto a slurry of ice, ammonium chloride and ether. The ether layer was separated and the aqueous layer re-extracted twice with more ether. The ether layers were washed three times with brine, combined and dried over sodium sulfate. A small sample of the ether solution upon evaporation yielded 2-(7-hydroxy-3-oxo-dodec-1-en-10-yl)-2,4,5-trimethyl-1,3-dioxolane as an oil, UV absolute maximum (in ethanol) at 208 m$\mu$,$\epsilon$ = 9,100.

The ether solution containing the δ-hydroxy vinyl ketone is treated with diethylamine (20 ml.) at room temperature for 3½ hours. Evaporation at 40° and 15 mm. Hg gave crude (±)-2,3-[6-hydroxy-6-(2-diethylaminoethyl)-2-tetrahydropyranyl]propyl)-2,4,5-trimethyl-1,3-dioxolane as an amber colored oil. After purification via acetic acid extraction, the aforesaid product was obtained as a pale yellow oil.

The starting material was prepared as follows. A total of 34.6 g. of (±)-6-(4,4-butylenedioxypentyl)-tetrahydropyran-2-ol was added to a stirred suspension of 346 g. of manganese dioxide in 1 liter of benzene at room temperature. After stirring for 16 hrs. at room temperature the solids were filtered off and washed well with more benzene. Removal of the benzene in vacuo and distillation of the residue yielded 16 g. of (±)-2-[3-(6-oxo-2-tetrahydropyranyl)-propyl]-2,4,5-trimethyl-1,3-dioxolane, b.p. 148°–150° at 0.03 mm.

EXAMPLE 4

A solution containing 4.3 g. of 5-hydroxy-5-[4-(t-butoxy)-pentyl]-valeric acid lactone in 25 ml. of tetrahydrofuran was cooled to −45° and a solution of 20 ml. of 20 percent vinyl magnesium chloride was then added over a period of 10 minutes. A total of 10 ml. of methanol was then added cautiously and the reaction mixture stirred for ten additional minutes. The reaction mixture was then poured onto a mixture comprising 200 g. of ice, 100 ml. of ether and 10 g. of ammonium chloride. This mixture was allowed to warm to 25° and the phases separated. Extraction of the aqueous phase with four portions totaling 250 ml. of ether, washing the combined ether extracts with brine and evaporation of the solvents yielded 5.0 g. of 7-hydroxy-3-oxo-11-t-butoxy-dodec-1-ene as a syrup.

To the above product dissolved in 50 ml. of ether was added 20 ml. of diethylamine. After evaporation of the ether and excess amine, the residue was again dissolved in 50 ml. of ether and extracted with cold 1N hydrochloric acid solution (4 × 30 ml.). The aqueous phases were neutralized with cold 1N sodium hydroxide and extracted with three portions of ether. The combined ether phases were dried over magnesium sulfate and evaporated to yield 5.2 g. of 2-(2-diethylaminoethyl)-2-hydroxy-6-(4-t-butoxy)-pentyl-tetrahydropyran as a syrup.

EXAMPLE 5

A solution of 10.0 g. (44.8 mmoles) of racemic 7-(3,5-dimethyl-4-isoxazolyl)-5-hydroxyheptanoic acid lactone in 150 ml. of freshly distilled tetrahydrofuran was cooled in a dry ice-isopropyl alcohol bath under nitrogen. A 25 percent (weight/volume) solution of vinyl magnesium chloride in tetrahydrofuran (25 ml., 75 mmoles) was added via syringe at a rate such that the temperature remained at approximately −60°. The mixture was stirred at −70° for 15 minutes, and then carefully hydrolyzed with 5 ml. of methanol. It was then poured onto a mixture of ice, 24 g. of ammonium chloride, and 8 ml. of acetic acid. The resulting solution was extracted with ether and the combined ether solutions were washed with water, saturated aqueous sodium bicarbonate solution, and saturated brine and dried over anhydrous sodium sulfate. After 10 minutes, 10 ml. of diethylamine was added to the ethereal solution of racemic 9-(3,5-dimethyl-4-isoxazolyl)-7-hydroxy-non-1-en-3-one. Ten minutes later, solvent removal gave crude racemic 2-(2-diethylaminoethyl)-6-[2-(3,5-dimethyl-4-isoxazolyl)ethyl]tetrahydropyran-2-ol as a light yellow oil. This material was taken up in ether and extracted with a total of 100 ml. of 1N hydrochloric acid followed by 25 ml. of water. The aqueous solutions were washed with ether and then placed under a layer of ether in an ice bath. The solution was made basic with 3N sodium hydroxide and then extracted with ether. The ether extracts were washed with water and saturated brine and dried over anhydrous sodium sulfate. Solvent removal gave the purified aforesaid Mannich base as a pale yellow oil.

The starting material may be prepared as follows. A solution of 320 ml. (325 g. = 2.5 moles) of ethyl acetoacetate, 209 ml. (178 g. = 2.5 moles) of pyrrolidine and 600 ml. of reagent grade benzene was heated at reflux with azeotropic removal of water for two hours. The benzene was then removed at reduced pressure and the residue was distilled through a 10-cm. Vigreux column yielding 427 g. of ethyl β-pyrrolidinocrotonate as a light yellow liquid, b.p. 155°–156°/10 mm.

A solution of the ethyl β-pyrrolidinocrotonate (427 g. = 2.33 moles), 190 ml. (182 g., 2.43 mole) of nitroethane and 1300 ml. of triethylamine in 1200 ml. of anhydrous chloroform was cooled in an ice bath under nitrogen. A solution of 235 ml. (393 g. = 2.56 mole) of phosphorus oxychloride in 400 ml. of chloroform was added at such a rate that the temperature did not rise above 15°. During the addition, which took place over a three-hour period, a viscous orange precipitate formed. This suspension was then stirred under nitrogen overnight. As much solvent as possible was removed at reduced pressure and the resulting red-brown paste was diluted with water and extracted with ether. The ether solutions were washed sequentially with water, 3N hydrochloric acid, water, 5 percent sodium hydroxide solution and water, and were dried over anhydrous sodium sulfate. Solvent removal at reduced pressure gave a dark oil which was distilled through a short Vigreux column to give 4-carboethoxy-3,5-dimethyl-isoxazole as a slightly cloudy, colorless liquid of b.p. 100°/11 mm.

A suspension of 100 g. (2.63 moles) of lithium aluminum hydride in 2.5 liters of anhydrous ether was stirred under nitrogen as a solution of 272 g. (1.61 mole) of the 4-carboethoxy-3,5-dimethylisoxazole prepared above in 400 ml. of anhydrous ether was added at such a rate as to maintain a gentle reflux. The suspension was stirred at room temperature under nitrogen overnight, during which time an extremely gummy green-gray mass formed in the bottom of the flask. The mixture was cooled in an ice bath and hydrolyzed with saturated aqueous sodium sulfate solution. Anhydrous sodium sulfate was added to dry the ether solution. The salts were removed by filtration and washed carefully with ether and chloroform. Solvent removal from the filtrates, finally at 50°/0.1 mm., gave a white crystalline mass. This was triturated with hot ether and then cooled. Filtration gave 3,5-dimethyl-4-hydroxy-methylisoxazole as white prisms, m.p. 76.5°–77.5°. Concentration of the mother liquors gave a second crop of prisms, m.p. 76.5°–78°.

A solution of 36.3 ml. (60.0 g., 0.5 mole) of thionyl chloride in 50 ml. of methylene chloride was cooled in an ice bath under a very slight negative pressure (for fume removal). A solution of 40.0 g. (0.314 mole) of 3,5-dimethyl-4-hydroxymethylisoxazole in 75 ml. of methylene chloride was added over 2½ hours. The resulting solution was stirred at room temperature for 2.0 hours. The solvent was removed at reduced pressure and the residue was distilled to give the desired chloride as a pale yellow liquid, b.p. 91.5°–93°/15 mm.

A solution of 59.6 g. (0.402 mole) of 4-chloromethyl-3,5-dimethylisoxazole, prepared as described above, and 116 g. (0.44 mole) of triphenylphosphine in 1 liter of toluene was heated at reflux under nitrogen for 6 hours. The resulting suspension was cooled and filtered. The filtrate was heated at reflux for an additional 20 hours. The precipitate was again removed by filtration and the combined solids were washed well with ether and benzene. The solvent was removed from the filtrate and the residue was taken up in 150 ml. of fresh toluene and refluxed for an additional 18 hours. Filtration as before gave another small quantity of solid. The combined solids were crystallized from ethanol-ether to give the desired phosphonium salt as a cream-white solid, m.p. 313°–316°.

A sample from a similar preparation was crystallized again from ethanol-ether to give analytically pure material as small white prisms, m.p. 303°–305°. (The melting point of this compound is dependent on the rate of heating.)

8.75 g. (0.20 mole) of 55 percent sodium hydride dispersion was washed under nitrogen with dry pentane to remove the mineral oil. To the flask was added 600 ml. of dimethylsulfoxide (dried over Linde 3A molecular sieves). The resulting suspension was carefully degassed, placed under nitrogen, and heated at 70°–75° for 1 hour. The gray-green solution was cooled to approximately 15° and 91.6 g. (0.20 mole) of (3,5-dimethyl-4-isoxazolylmethyl) triphenylphosphonium chloride, prepared as described above, was added in one portion. After approximately 5 minutes, a bright orange precipitate formed in the initially dark red solution. This suspension was stirred at room temperature for 45 minutes. To the mixture was then added, dropwise via syringe, 25.0 g. (0.223 mole) of acrolein dimer (freshly distilled from and into hydroquinone) at such a rate that the temperature remained less than 30° (10–15 minutes with water bath cooling). The light orange-brown solution was stirred at room temperature for 20 minutes, and then at 60°–65° for 3 hours. (In some experiments, the mixture became very black during the heating period.) The reaction mixture was cooled, poured onto ice, and slurried until all of the dark oil solidified. The suspension was filtered and the filter cake was washed well with pentane. The filtrates were extracted with pentane and the pentane solutions were washed with water and brine and dried over anhydrous sodium sulfate. Solvent removal gave a slightly orange oil which was distilled from a small quantity of anhydrous potassium carbonate to give the desired product as a colorless liquid, b.p. 83°–85°/0.1 mm.

To a solution of 33.5 g. (0.163 mole) of 3,5-dimethyl-4-(3,4-dihydro-2H-pyran-2-ylvinyl)-isoxazole, prepared as described above, in 400 ml. of dioxane, was added 400 ml. of 1N sulfuric acid and the cloudy solution, which soon cleared, was stirred at room temperature for 1 hour. The mixture was poured into 2 liters of saturated aqueous sodium bicarbonate solution and extracted well with ether. The ether extracts were washed with brine and dried over anhydrous sodium sulfate. Solvent removal gave a colorless oil, the infrared spectrum of which indicated that complete hydration of the enol ether had taken place. This material was taken up in 2 liters of benzene and placed under nitrogen. To the flask was added 400 g. of manganese dioxide and the resulting suspension was stirred at room temperature for 40 hours. The manganese dioxide was removed by filtration and carefully washed with fresh benzene. Solvent removal from the filtrate gave 23 g. of yellow solid. Two crystallizations of this material from benzene-ether gave the desired lactone as a cream-white powder, m.p. 90.0°–91.5°.

A mixture of 16.80 g. (76.0 mmoles) of racemic 7-(3,5-dimethyl-4-isoxazolyl)-5-hydroxy-$\Delta^6$-heptenoic acid lactone prepared as above, 400 ml. of ethylacetate, and 500 mg. of 10 percent palladium on carbon was hydrogenated at room temperature and atmospheric pressure. Uptake (1.25 × theoretical) was rapid and ceased after 2 hours. The catalyst was removed by filtration and washed with fresh ethyl acetate. Solvent removal gave a colorless oil which was crystallized from ether at −20° to give the desired product as white microprisms of m.p. 61°–62.5°.

To a solution of 1.0 g. (4.88 mmoles) of 3,5-dimethyl-4-(3,4-dihydro-2H-pyran-2-ylvinyl) isoxazole, prepared as described above, in 10 ml. of ethanol was added 5 drops of 1N sulfuric acid. The solution was stirred at room temperature overnight, poured into excess saturated aqueous sodium bicarbonate solution, and extracted with ether. The ether extracts were washed with water and saturated brine and dried over anhydrous sodium sulfate. Solvent removal gave 1.25 g. of pale yellow liquid whose infrared spectrum indicated that formation of racemic 3,5-dimethyl-4-(6-ethoxytetrahydropyran-2-ylvinyl)-isoxazole was complete. This material was taken up in 10 ml. of ethyl acetate. To this solution was added 25 mg. of 10 percent palladium on carbon and the resulting mixture was hydrogenated at room temperature and atmospheric pressure. After 2 hrs., one equivalent of hydrogen had been consumed and uptake ceased. The catalyst was removed by filtration and washed with fresh ethyl acetate. Solvent removal from the filtrates gave 1.28 g. of racemic 3,5-dimethyl-4-(6-ethoxytetrahydropyran-2-ylethyl)-isoxazole as a colorless oil whose infrared spectrum indicated that the hydrogenation was complete. This crude acetal was taken up in 20 ml. dioxane. To the flask was added 10 ml. of 1N sulfuric acid and the resulting solution was stirred at room temperature for 4 hrs. It was then poured into excess saturated aqueous sodium bicarbonate solution and extracted with ether. The ether extracts were washed with saturated brine and dried over anhydrous sodium sulfate. Solvent removal gave racemic 3,5-dimethyl-4-(6-hydroxytetrahydropyran-2-ylethyl)-isoxazole as a viscous oil. The crude hemiketal was taken up in 25 ml. of 1,2-dichloroethane, degassed and placed under nitrogen. To the flask was added 7.5 g of manganese dioxide and the resulting suspension was stirred at room temperature overnight. The manganese dioxide was removed by filtration and washed with fresh solvent. Solvent removal from the filtrates gave a pale yellow resin which was crystallized from ether at −20° C. to give the desired lactone, 3,5-dimethyl-4-(6-hydroxytetrahydropyran-2-ylethyl)-isoxazole, as a white solid of m.p. 60°–62°.

A solution of 3,5-dimethyl-4-(6-hydroxytetrahydropyran-2-ylethyl)-isoxazole, prepared as described above in 600 ml. of acetone was cooled in an ice bath as 400 ml. of Jones reagent was added dropwise over a 1.0 hr. period. The resulting suspension was stirred at room temperature overnight. Saturated sodium bisulfite solution was added to destroy the excess oxidizing agent and most of the acetone was removed at reduced pressure. The residue was diluted with water, saturated with sodium chloride, and extracted with ethyl acetate. The ethyl acetate solutions were washed with brine and then with excess saturated aqueous sodium bicarbonate solution. The sodium bicarbonate solutions were washed with ether, acidified with 3N hydrochloric acid, saturated with sodium chloride, and extracted with ethyl acetate. The ethyl acetate solutions were washed with brine and dried over anhydrous sodium sulfate. Solvent removal at reduced pressure gave a pale yellow resin. Crystallization of this material from ether gave two crops of racemic 7-(3,5-dimethyl-4-isoxazolyl)-5-oxo-heptanoic acid as a fine white powder, m.p. 61.5°–63.5°.

A solution of the keto acid prepared above (41.2 g., 0.178 mole) in 600 ml. of isopropyl alcohol was placed under nitrogen. To this solution was carefully added 10.0 g. (0.296 mole) of sodium borohydride. After the initial vigorous reaction had subsided, the cloudy solution was heated at reflux overnight. A major portion of the solvent was then removed at reduced pressure. The residue was diluted with water, acidified with 1N hydrochloric acid, saturated with salt, and extracted with ether. The ether solutions were washed with brine and dried over anhydrous sodium sulfate. Solvent removal at reduced pressure gave racemic 7-(3,5-dimethyl-4-isoxazolyl)-5-hydroxyheptanoic acid as a cloudy colorless resin. This material was heated to 220°/0.3 mm., at which time a colorless liquid rapidly distilled. Crystallization from ether gave the desired lactone as white prisms, m.p. 61°–63°.

EXAMPLE 6

1.6 g. of the ketal lactone, (±)-9,9-phenylenedioxy-5-hydroxy-decanoic acid lactone in tetrahydrofuran (THF; 15 ml.) was cooled to −45° and treated over 5 minutes with a solution of vinyl magnesium chloride in THF (4.6 ml.; 2 mol/liter). After stirring a further 25 min., at −45°, methanol (5 ml.) was added followed by an aqueous ammonium chloride solution (15 percent; 20 ml.). The products were extracted into ether and the ether extracts then treated with diethylamine (5 ml.) and dried over magnesium sulfate. Removal of the solvents in vacuo gave the crude Mannich base which was separated from neutral material with dilute aqueous acid (1N.H₂SO₄; 4 × 15 ml.). The aqeuous extracts were made basic with caustic potash solution and the products isolated with ether. Removal of the solvents in vacuo gave the Mannich base, (±)-6-(4,4-phenylenedioxypentyl)-2-(2-diethylaminoethyl)-tetrahydropyran-2-ol as a mobile liquid.

This material showed one spot on tlc analysis on development with a benzene/triethylamine (9:1) system.

The starting material may be prepared as follows. 25 g. of the hemiacetal, (±)-6-[3-(2-methyl-1,3-dioxolan-2-yl)propyl]tetrahydropyran-2-ol was dissolved in a mixture of dimethylformamide (120 ml.), acetic acid (40 ml.), water (120 ml.) and sodium acetate (anhydrous) (24 g.). Bromine (7 ml.) was then added to the cold (5–10°) solution over 2–5 min. and the mixture was then stirred for a further 45 min. at room temperature. Aqueous sodium bisulfite solution and brine were then added and the organic products were isolated with benzene (5 × 125 ml.). The benzene extracts were washed with saturated brine solution (5 × 50 ml.) and taken to dryness in vacuo. The crude lactone, (±)-9,9-ethylenedioxy-5-hydroxy-decanoic acid lactone yielded pure material on distillation, b.p. 138°–140°/.02 mm.

52.4 g. of the ketal lactone (±)-9,9-ethylenedioxy-5-hydroxydecanoic acid lactone dissolved in acetone (150 ml.) was treated with water (75 ml.), dilute aqueous sulfuric acid (2N; 45 ml.) and left to stand at room temperature for 16 hrs. Addition of brine and extraction with benzene gave the crude lactone, (±)-9-oxo-5-hydroxydecanoic acid lactone which was purified by distillation, b.p. 134°/.05 mm.

15 g. of a solution of the ketolactone (±)-9-oxo-5-hydroxydecanoic acid lactone in benzene (300 ml.) was treated with 20 g. catechol and 0.6 g. of p-toluenesulfonic acid. The mixture was heated at reflux under nitrogen in conjunction with a soxholet extraction apparatus equipped with a thimble filled with calcium hydride. After 18 hrs. at reflux the mixture was cooled and chromatographed directly on silica gel (0.2–0.5 mm mesh; 650 g.). Elution with 5 percent, 10 percent and 15 percent ethyl acetatebenzene mixtures yielded the ketal ester 9,9-phenylenedioxy-5-hydroxy-decanoic acid 2-hydroxyphenylester.

Distillation of the above material gave catechol and the desired lactone, (±)-9,9-phenylendioxy-5-hydroxy-decanoic acid lactone, b.p. 152°–170°/.2 mm. (This was a short path distillation and the majority of the material had b.p. 157°–162°.) A sample of this material was redistilled (Kugel Rhor) and gave purified lactone, b.p. 140°–145°/.02 mm.

I claim:
1. The process wherein a compound of the formula

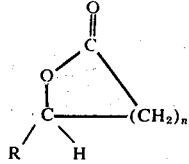

where n is an integer from 2 to 4, R is hydrogen, alkyl having from 1 to 15 carbon atoms or alkyl substituted with one of the following: oxo; ketal protected oxo; hydroxy; lower acyloxy; lower alkoxy or when said alkyl is ethyl, substituted on the β-carbon atom with an isoxazole ring of the formula

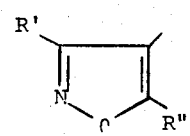

wherein R' is lower alkyl or hydrogen and R'' is lower alkyl, lower alkyl phenyl, or hydrogen is reacted with a vinyl Grignard at a temperature below about 0° C to produce a compound of the formula

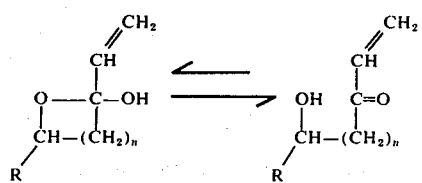

where R and n are as above.
2. The process of claim 1 wherein the temperature is in the range of from about −90° C. to about 0° C.
3. The process of claim 1 wherein n is 3.
4. The process of claim 1 wherein R is alkyl having from 1 to 15 carbon atoms.
5. The process of claim 4 wherein R is ethyl.
6. The process of claim 1 wherein R is alkyl substituted with a ketal protected oxo group.
7. The process of claim 6 wherein R is 4,4-(2,3-butylenedioxy)-pentyl.
8. The process of claim 6 wherein R is 4,4-(1,2-ethylenedioxy)-pentyl.
9. The process of claim 6 wherein R is 4,4-phenylenedioxypentyl.
10. The process of claim 1 wherein R is alkyl substituted with lower alkoxy or lower acyloxy.
11. The process of claim 10 wherein R is 4-t-butoxypentyl.
12. The process of claim 1 wherein R is ethyl substituted with said isoxazolyl group.
13. The process of claim 12 wherein R is 2-(3,5-dimethyl-4-isoxazolyl)-ethyl.
14. The process of claim 1 wherein said vinyl Grignard is vinyl magnesium chloride.
15. The process of claim 1 wherein the product produced therein is stabilized by reaction with an amine of the formula

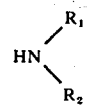

wherein $R_1$ taken independently is hydrogen or lower alkyl; $R_2$ taken independently is lower alkyl or phenyl lower alkyl; and $R_1$ and $R_2$ taken together with the adjacent nitrogen atom form a 5 or 6 membered saturated hetero cyclic ring selected from the group consisting of piperidino, pyrrolidino and morpholino.

16. The process of claim 15 wherein said amine is a di-lower alkylamine, e.g., $R_1$ and $R_2$ both are lower alkyl.

17. The process of claim 16 wherein said amine is diethylamine, e.g., $R_1$ and $R_2$ are both ethyl.

* * * * *